United States Patent
Henry

(10) Patent No.: US 11,839,826 B2
(45) Date of Patent: Dec. 12, 2023

(54) MODULAR FIELD MANIPULATION APPARATUS AND METHOD OF MANUFACTURING SAME

(71) Applicant: Aaron James Henry, Mattawan, MI (US)

(72) Inventor: Aaron James Henry, Mattawan, MI (US)

(73) Assignee: Aaron James Henry, Mattawan, MI (US)

( * ) Notice: Subject to any disclaimer, the term of this patent is extended or adjusted under 35 U.S.C. 154(b) by 0 days.

(21) Appl. No.: 17/686,516

(22) Filed: Mar. 4, 2022

(65) Prior Publication Data

US 2023/0277921 A1 Sep. 7, 2023

(51) Int. Cl.
*A63F 9/06* (2006.01)
*A63F 9/00* (2006.01)
*A61N 2/00* (2006.01)

(52) U.S. Cl.
CPC ............ *A63F 9/06* (2013.01); *A61N 2/006* (2013.01); *A63F 9/0096* (2013.01); *A63F 2250/02* (2013.01); *A63F 2250/26* (2013.01); *A63F 2250/48* (2013.01)

(58) Field of Classification Search
CPC .. A63F 9/06; A63F 9/0096; A63F 9/34; A63F 2003/0063; A61N 2/006; A63H 33/26; A63H 33/046
See application file for complete search history.

(56) References Cited

U.S. PATENT DOCUMENTS

| | | | | |
|---|---|---|---|---|
| 4,011,674 A | * | 3/1977 | Jacobson | A63H 33/26 446/131 |
| 7,892,065 B2 | | 2/2011 | Vicentelli | |
| 10,173,143 B2 | | 1/2019 | Ferguson | |
| 10,449,466 B2 | | 10/2019 | Kinmont, Jr. | |
| 2002/0115373 A1 | | 8/2002 | Lazerman | |
| 2010/0087119 A1 | * | 4/2010 | Vicentelli | A63H 33/046 446/92 |
| 2014/0213139 A1 | * | 7/2014 | Ferguson | A63H 33/046 446/92 |
| 2015/0258461 A1 | | 9/2015 | Balanchi | |
| 2015/0367242 A1 | * | 12/2015 | Calello | A63H 17/002 446/465 |

(Continued)

FOREIGN PATENT DOCUMENTS

| | | |
|---|---|---|
| WO | 2004089493 | 10/2004 |
| WO | 2019043698 | 3/2019 |

*Primary Examiner* — Christine H Matthews
(74) *Attorney, Agent, or Firm* — Caldwell Intellectual Property Law, LLC

(57) ABSTRACT

In an aspect a modular field manipulation apparatus is presented. A modular field manipulation apparatus includes a central field manipulation device. A central field manipulation device includes a first surface having a first field polarity. A central field manipulation device includes a second surface positioned opposite a first surface. A second surface includes a second field polarity. A modular field manipulation apparatus includes a plurality of interconnecting components. Each interconnecting component of a plurality of interconnecting components includes at least a contacting member. At least a contacting member engages with at least a first surface of a central field manipulation device.

5 Claims, 13 Drawing Sheets

(56) References Cited

U.S. PATENT DOCUMENTS

| | | | |
|---|---|---|---|
| 2017/0319978 A1 | 11/2017 | Pacheco | |
| 2018/0345156 A1 | 12/2018 | Bornstein | |
| 2019/0021282 A1* | 1/2019 | Wilhelm | A63H 15/06 |
| 2019/0021285 A1* | 1/2019 | Chen | A01K 15/027 |
| 2019/0336404 A1* | 11/2019 | Gastle | A63H 33/006 |
| 2019/0358559 A1 | 11/2019 | Bennett | |
| 2021/0023470 A1 | 1/2021 | Eifes et al. | |

* cited by examiner

US 11,839,826 B2

MODULAR FIELD MANIPULATION APPARATUS AND METHOD OF MANUFACTURING SAME

FIELD OF THE INVENTION

The present invention generally relates to the field of modular field manipulation devices. In particular, the present invention is directed to a modular apparatus and system for alleviating symptoms of neurodivergence.

BACKGROUND

Modern apparatuses and systems for alleviating symptoms of neurodivergence, such as attention deficit hyperactivity disorder (ADHD), tend to have only one mode of operation. As such, neurodivergent individuals may lose interest with these systems and apparatuses which may lead to increased symptoms of neurodivergence.

SUMMARY OF THE DISCLOSURE

In an aspect a modular field manipulation apparatus is presented. A modular field manipulation apparatus includes a central field manipulation device. A central field manipulation device includes a first surface having a first field polarity. A central field manipulation device includes a second surface positioned opposite a first surface. A second surface includes a second field polarity. A modular field manipulation apparatus includes a plurality of interconnecting components. Each interconnecting component of a plurality of interconnecting components includes at least a contacting member. At least a contacting member engages with at least a first surface of a central field manipulation device. A plurality of interconnecting components includes at least one interconnecting component including a component configured to interact with a central field manipulation device.

In another aspect a system for alleviating symptoms of neurodivergence is presented. A system includes a first engagement device. A first engagement device includes a first surface having a first field polarity. A first engagement device includes a second surface positioned opposite a first surface. A second surface includes a second field polarity. A first engagement device includes a grasping element. A system includes a plurality of engagement device modifiers. Each engagement device modifier of a plurality of engagement device modifiers includes at least a contacting member. At least a contacting member engages with at least a first surface of a first engagement device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Described herein is a modular field manipulation apparatus. A modular field manipulation apparatus may include a central field manipulation device. A central field manipulation device may include a first surface having a first field polarity. A central field manipulation device may include a second surface positioned opposite a first surface. A second surface may include a second field polarity. A modular field manipulation apparatus may include a plurality of interconnecting components. Each interconnecting component of a plurality of interconnecting components may include at least a contacting member. At least a contacting member may engage with at least a first surface of a central field manipulation device.

Described herein is a system for alleviating symptoms of neurodivergence. A system may include a first engagement device. A first engagement device may include a first surface having a first field polarity. A first engagement device may include a second surface positioned opposite a first surface. A second surface includes a second field polarity. A first engagement device may include a grasping element. A system may include a plurality of engagement device modifiers. Each engagement device modifier of a plurality of engagement device modifiers may include at least a contacting member. At least a contacting member may engage with a first engagement device to provide an interaction for a user of the first engagement device.

Figure 1:
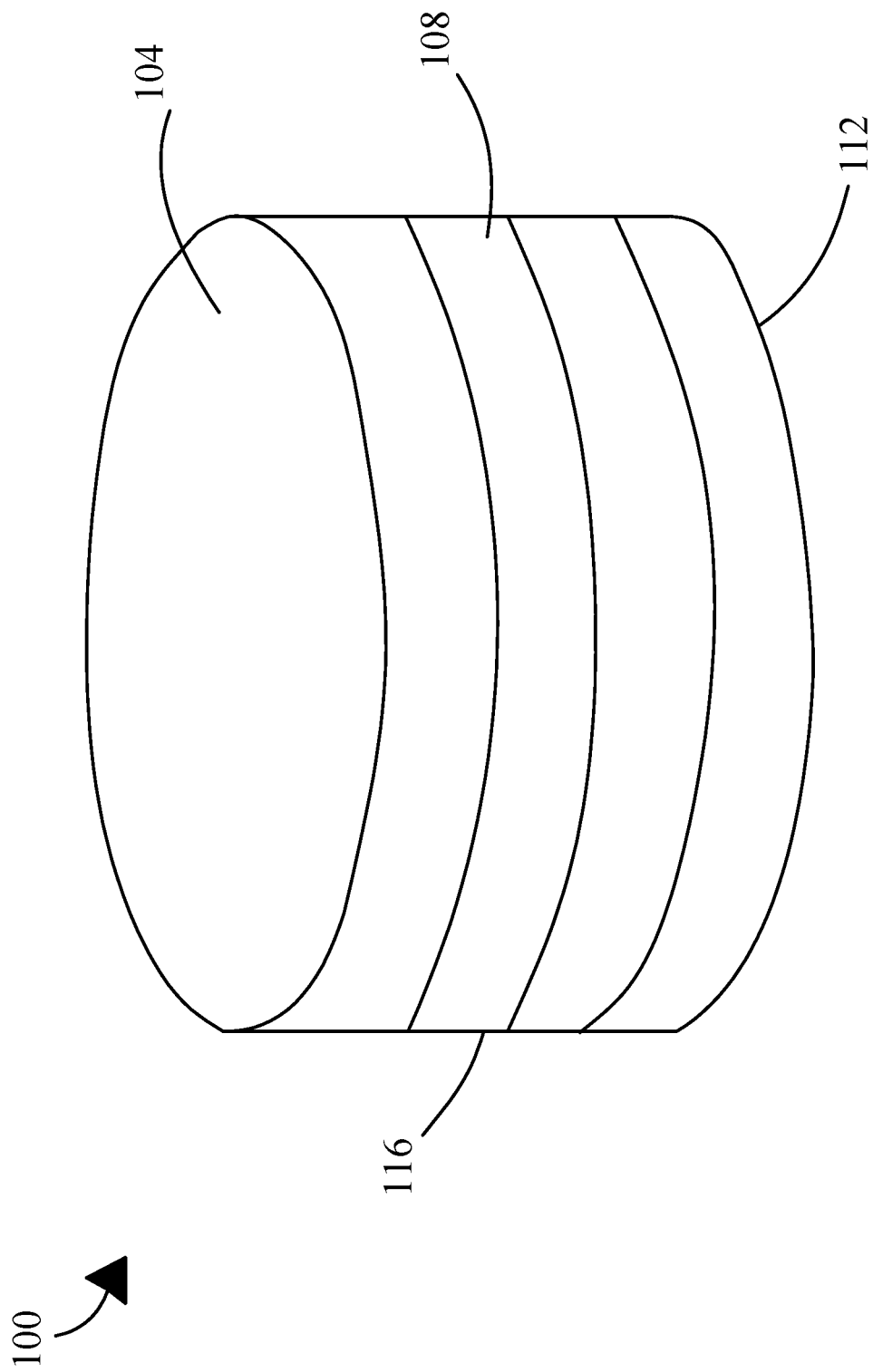
FIG. 1 is an exemplary embodiment of a central field manipulation device.

Referring now to the drawings, FIG. 1 illustrates an exemplary embodiment of a modular field apparatus. A modular field apparats includes central field manipulation device 100. A "central field manipulation device" as used in this disclosure is any object that is configured to interact with at least one external field. Central field manipulation device 100 may be configured to interact with one or more interconnecting components as described below. An "interconnecting component" as used in this disclosure is any object configured to interact with one or more other objects. Each interconnecting component may be configured to engage with central field manipulation device 100 in a variety of ways. Interconnecting components may be modular, such that central field manipulation device 100 may be configured to perform one or more modes of operation when engaged with an interconnecting component. Engaging central field manipulation device 100 with an interconnecting component may help reduce symptoms of neurodivergence. "Neurodivergence" as used in this disclosure is any variation in a human brain regarding sociability, learning, attention, mood, and/or other mental functions in a non-pathological sense. Neurodivergence may include conditions such as, but not limited to, ADHD, autism, dyslexia, Tourette's, and the like. Symptoms of neurodivergence may include, but are not limited to, difficulty concentrating, impulsive behavior, restless leg syndrome, irritability, racing thoughts, feelings of being overwhelmed, trouble communicating, and the like. By engaging with central field manipulation device 100 and an interconnecting component, an individual with neurodivergence, such as ADHD, may be able to release nervous energy, which may increase focus. Central field manipulation device 100 may be used as a coping mechanism and/or cognitive skill development tool for users without neurodivergence or other cognitive deficiencies. In some embodiments, engaging central field manipulation device 100 may provide a way for a user to fidget with central field manipulation device 100 and regulate stress. Engaging with central field manipulation device 100 may provide a user with a self-stimulating outlet that may reduce stress levels of the user. In some embodiments, engaging with central field manipulation device 100 may provide for physical therapy and/or occupational therapy. Physical and/or occupational therapies may include, but are not limited to, fine motor control therapy, manual dexterity therapy, sensory processing therapy, and the like. As such, a system for cognitive skill development and coping strategies is described herein.

Still referring to FIG. 1, in some embodiments, central field manipulation device 100 may have a shape. A shape may include 3-Dimensional (3D) shapes such as, but not limited to, cylinders, cubes, boxes, and the like. A shape may include a cross-sectional shape. A cross-sectional shape may include any combination of curved and/or polygonal forms. Any surface of central field manipulation device 100 may include any shape suitable for a cross-sectional shape. A shape may include, but is not limited to, a cylinder, circle, oval, rectangle, square, triangle, cube, and the like. In some embodiments, central field manipulation device 100 may include top portion 104. A "top portion" as used in this disclosure is an area portion, point, and/or surface of an object greater in height than the rest of the object. Top portion 104 may include a section of central field manipulation device 100 that may be above middle portion 108 of central field manipulation device 100. A "middle portion" as used in this disclosure is an area portion, point, and/or surface of an object between a highest area and a lowest area of the object. Middle portion 108 of central field manipulation device 100 may include a section of central field manipulation device 100 that may be between top portion 104 and bottom portion 112. A "bottom portion" as used in this disclosure is an area portion, point, and/or surface of an object lowest in height than the rest of the area of the object. Bottom portion 112 of central field manipulation device 100 may include a section of central field manipulation device 100 that may be positioned beneath middle portion 108 and top portion 104 of central field manipulation device 100. In some embodiments, central field manipulation device 100 may include one or more dimensions. A "dimension" as used in this disclosure is any measurement of an object. Dimensions may include, but are not limited to, height, length, width, volume, thickness, and the like. In some embodiments, central field manipulation device 100 may include a uniform shape such that each portion of central field manipulation device 100 may include a same dimension such as, but not limited to, length, circumference, width, and the like. A uniform shape may include, but is not limited to, a cylindrical shape, cubical shape, spherical shape, and the like. In other embodiments, central field manipulation device 100 may include a non-uniform shape. A non-uniform shape may include a shape such that at least two sections of central field manipulation device 100 may have varying dimension values. A non-uniform shape may include, but is not limited to, a concave shape, a convex shape, a twisted structure, and the like.

Still referring to FIG. 1, in some embodiments, Central field manipulation device 100 may include field generating component 116. A "field" as used in this disclosure is any area in which a force acts upon one or more objects. A field may include, but is not limited to, a magnetic field, an electric field, and the like. A magnetic field may include a vector field that may describe a magnetic influence on, but not limited to, electric charges, electric currents, magnetic materials, and the like. Field generating component 116 may include magnetic materials such as, but not limited to, permanent magnetic materials, temporary magnetic materials, and/or electromagnets. Magnetic materials may include, but are not limited to, ferrous materials, diamagnetic materials, paramagnetic materials, ferrimagnetic materials, rare earth magnets, neodymium magnets, and/or anti ferromagnetic materials. Field generating component 116 may materials such as, but not limited to, iron, nickel, cobalt, gadolinium, dysprosium, terbium, ferritic stainless steel, neodymium, boron alloys, and the like. In some embodiments, field generating component 116 may include two or more field generating components. Two or more field generating components may include a same magnetic material, different magnetic material and/or a combination thereof. Field generating component 116 may include one or more magnets, such as, but not limited to, bar magnets, ball magnets, disk magnets, and the like. In some embodiments, field generating component 116 may be configured to generate a field, such as, but not limited to, a magnetic field. A magnetic field may include a dipole magnetic field. A dipole magnetic field may have a first polarity and a second polarity, such as a north pole and a south pole. In some embodiments, a first polarity may oppose a magnetic field of a same polarity, while attracting a magnetic field of an opposite polarity. As a non-limiting example, a north pole generated by field generating component 116 may oppose another north pole of another magnetic field. Field generating component 116 may include a magnetic moment. A magnetic moment may include a vector that may characterize a magnet's magnetic properties. A magnetic moment may be measured in terms of amperes times meters squared, or $A \cdot m^2$. A magnetic field of a dipole magnet may include a magnetic field originating from a north pole of the dipole magnet and wrapping around to a south pole of the dipole magnet. A magnetic field may be measured by magnetic flux density, denoted B. A magnetic field B may include a direction and a magnitude. A magnetic field B may be measured in terms of strength by a unit known as a Tesla (T).

A Tesla may be defined as a strength of magnetic field as measured in units of velocity times seconds over meters squared V·s/m$_2$.

Still referring to FIG. 1, field generating component 116 may be configured to apply a first field polarity to a first surface of central field manipulation device 100. A "first surface" as used in this disclosure is an exterior face of an object. A first surface may include top portion 104. Field generating component 116 may apply a north pole to a first surface of central field manipulation device 100. In some embodiments, field generating component 116 may apply a second field polarity to a second surface of central field manipulation device 100. A "second surface" as used in this disclosure is any region of an object different from a first region. A second surface may include bottom portion 112. A second surface may be positioned opposite a first surface. A second surface may be stacked on or below a first surface. Field generating component 116 may apply a south pole to a second surface of central field manipulation device 100. In some embodiments, a second surface of central field manipulation device 100 may be opposite a first surface of central field manipulation device 100. Field generating component 116 may be configured to apply a field to central field manipulation device 100 such that central field manipulation device 100 may act as a dipole magnet. Central field manipulation device 100 may have a north pole at top portion 104 and/or a south pole at bottom portion 112. A magnetic field may travel from a north pole of top portion 104 around central field manipulation device 100 to a south pole of bottom portion 112. In some embodiments, central field manipulation device may include two or more field generating components 116 stacked on top one another.

Still referring to FIG. 1, in some embodiments central field manipulation device 100 may include a casing. A "casing" as used in this disclosure is any material that surrounds at least a portion of an object. A casing may include a non-field generating material, such as, but not limited to, wood, plastic, rubber, and the like. In some embodiments, a casing may include two or more subcasings. For instance and without limitation, a casing may include a first subcasing of wood which may completely surround field generating components 116. A second subcasing may include an epoxy which may be positioned between field generating components 116 and a first subcasing of wood. In some embodiments, a casing may include three or more subcasings. A subcasing may surround at least a portion of one or more field generating components 116. In some embodiments, a subcasing may completely surround field generating components 116. In some embodiments, a casing of central field manipulation device 100 may include an epoxy completely surrounding field generating components 116. An epoxy may provide structural stability to one or more field generating components 116. Structural stability may include securing one or more field generating components 116 in a fixed position.

Figure 2:
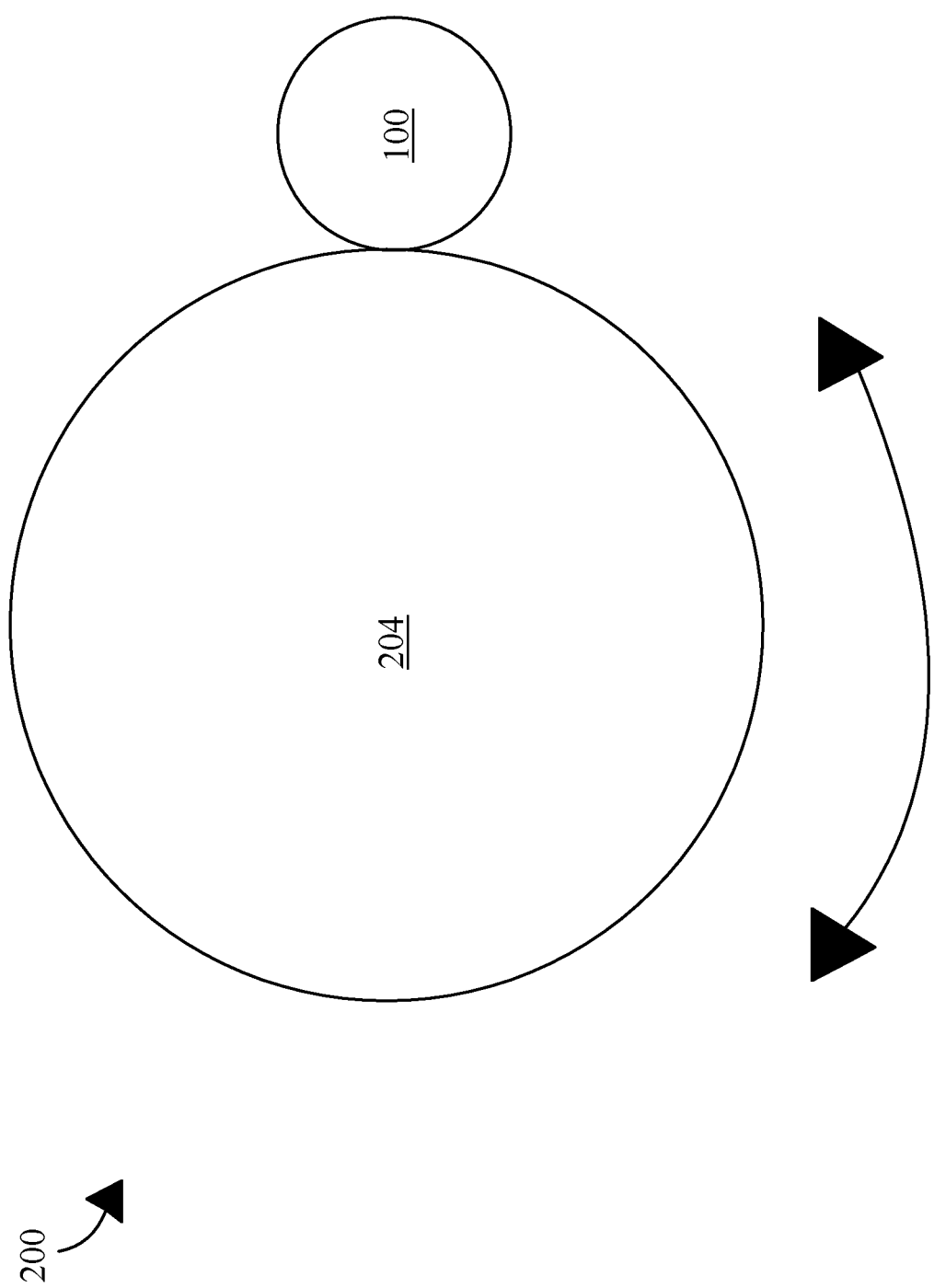
FIG. 2 is an exemplary embodiment of a modular field manipulation apparatus showing a revolving configuration.

Referring now to FIG. 2, an exemplary embodiment of a modular field manipulation apparatus 200 is shown. Apparatus 200 may include interconnecting component 204. Interconnecting component 204 may include a shape, such as, but not limited to, a circle, cylinder, and the like. Interconnecting component 204 may include a dimension greater than that of central field manipulation device 100. Interconnecting component 204 may include a circumference, surface area, radius, thickness, height, volume, and the like. Interconnecting component 204 may include a ratio of a dimension to a dimension of central field manipulation device 100. As a non-limiting example, interconnecting component 204 may include a ratio of about 5:1 to about 10:1 of a circumference to a circumference of central field manipulation device 100. In some embodiments, interconnecting component 204 may include a ratio of less than about 5:1 of a circumference to a circumference of central field manipulation device 100. Interconnecting component 204 may include a contacting member. A "contacting member" as used in this disclosure is any area of an object designed to engage with an area of one or more other objects. A contacting member may include, but is not limited to, a planar surface, a curved surface, a convex surface, a concave surface, a protruding surface, a bearing, an edge, and the like. Interconnecting component 204 may include a contacting surface in a form of a circular surface, such as a circumference of interconnecting component 204. Interconnecting component 204 may include a magnetic field generating component. A magnetic field of interconnecting component 204 may have an opposite polarity of a field of central field manipulation device 100. A field of central field manipulation device 100 may interact with a field of interconnecting component 204. Interaction may include modifying an alignment of a field of central field manipulation device 100. As a non-limiting example, a field of central field manipulation device 100 may include a uniform alignment of a magnetic field. Interconnecting component 204 may include a magnetic field of a same or opposite polarity, which may align with or misalign with a field of central field manipulation device 100. A field of central field manipulation device 100 may oppose a same polarity field of interconnecting component 204 which may cause the field of central field manipulation device 100 to align against the field of interconnecting component 204. A field of central field manipulation device 100 may attract a field of an opposite polarity of interconnecting component 204, which may cause the field of central field manipulation device 100 to align with the field of interconnecting component 204. Interaction may include a pulling force between a field of central field manipulation device 100 and a field of interconnecting component 204. A pulling force between two magnetic fields may be defined by $F=\mu q_{m1}*\mu q_{m2}/4\pi r^2$. In some embodiments, interconnecting component 204 may be configured to pull central field manipulation device 100 to a side of interconnecting component 204. Interconnecting component 204 may be configured to secure central field manipulation device 100 on a side of interconnecting component 204 such that central field manipulation device 100 may attach to interconnecting component 204 without physical support. Interconnecting component 204 may include a magnetic field that may surround a circumference of interconnecting component 204. Central field manipulation device 100 may be configured to pull around a circumference of interconnecting component 204 through magnetic forces. Central field manipulation device 100 may be configured to revolve around a revolving axis of interconnecting component 204. A "revolving axis" as used in this disclosure is an axis about which an object revolves. Central field manipulation device 100 may revolve around a revolving axis, such as but not limited to an x-axis of interconnecting component 204 in a clockwise and/or counterclockwise manner. In some embodiments, interconnecting component 204 may include a top surface and/or bottom surface that may include a gripping element. A "gripping element" as used in this disclosure is any material and/or structure that assists with a gripping of an object. A gripping element may include, but is not limited to, indented structures, ribbed structures, rough surface materials, and the like. In some embodiments, a gripping element may include a dimension such as, but not limited to, height, width, length, surface area, and the like. A gripping element may include a dimension having a surface area similar in size to an average human hand, thumb, pointer finger, and the like. Interconnecting component 204 may include a gripping element that may assist in a user engaging with apparatus 200. A user may hold interconnecting component 204 and apply a torque to central field manipulation device 100 through moving interconnecting component 204 in a circular motion, which may allow central field manipulation device 100 to revolve around interconnecting component 204. In some embodiments, a vibration of air may be produced by central field manipulation device 100 rubbing a surface of interconnecting component 204, such as a vibrating member. A "vibrating member" as used in this disclosure is any object part and/or object designed to vibrate. A vibrating member may include, but is not limited to, a rod, string, whistle, and the like. A vibrating member may produce air vibrations. A vibration of air may produce a musical tone. A "musical tone" as used in this disclosure is any melodic sound. In some embodiments, interconnecting component 204 may include a whistle and/or other device which may be configured to more clearly produce a musical tone. By engaging with apparatus 200, an individual with neurodivergence, such as ADHD, may be able to release nervous energy, which may increase focus.

Figure 3:
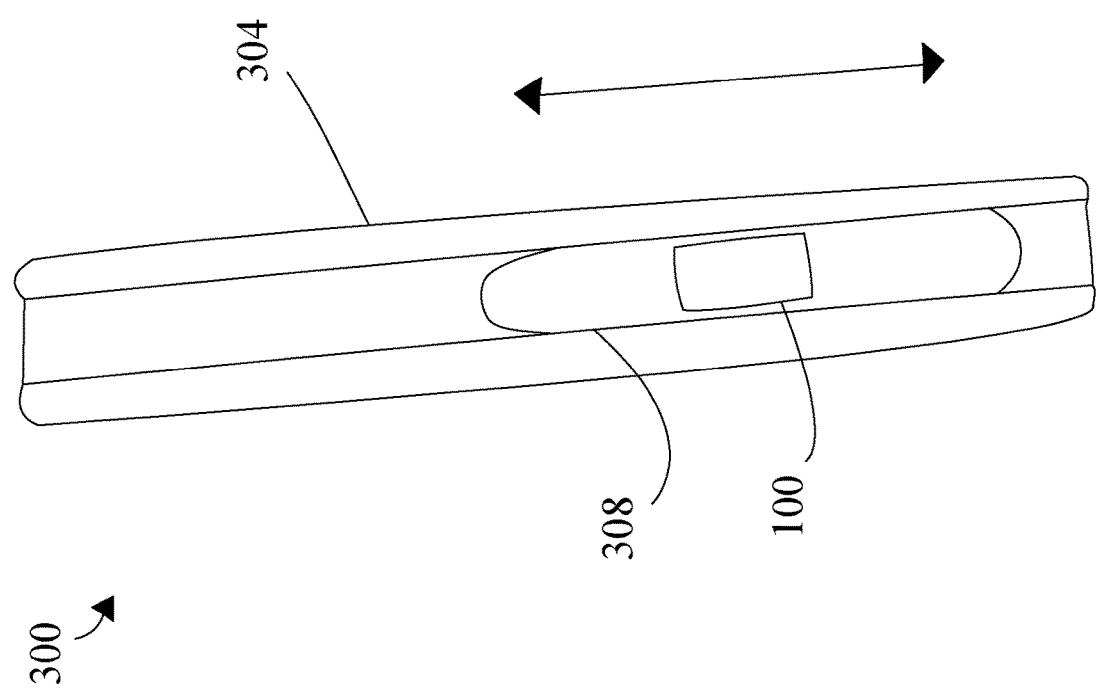
FIG. 3 is another exemplary embodiment of a modular field manipulation apparatus showing an oscillating configuration.

Referring now to FIG. 3, another exemplary embodiment of a modular field manipulation apparatus 300 is presented. Apparatus 300 may include interconnecting component 304, which may include any interconnecting component as described above. Interconnecting component 304 may include a shape, such as, but not limited to, rectangular, circular, and the like. In some embodiments, interconnecting component 304 may include a rigid material, such as, but not limited to, wood, plastic, and the like. Interconnecting component 304 may include recess 308. A "recess" as us used in this disclosure is any indentation in an object. Recess 308 may include a dimension. A dimensions of recess 308 may include, but is not limited to, length, width, depth, diameter and the like. Recess 308 may be configured to support top portion 104, bottom portion 112, and/or middle portion 108 of central field manipulation device 100. Recess 308 may be configured to physically support central field manipulation device 100. Recess 308 may be configured to direct a movement of central field manipulation device 100. In some embodiments, recess 308 may direct central field manipulation device 100 in a linear path from a first end of recess 308 to a second end of recess 308. Interconnecting component 304 may include one or more field generating components. In some embodiments, a first field generating component having a first polarity may be positioned within a first end of recess 308. A second field generating component having a second polarity may be positioned within a second end of recess 308. Recess 308 may be configured to oscillate central field manipulation device 100 between a first end of recess 308 and a second end of recess 308 through opposing magnetic fields. As a non-limiting example, a first magnetic field of recess 308 may include a north pole, and a second end of recess 308 may include a south pole. Central field manipulation device 100 may align a north pole with a north pole of recess 308, causing an opposing force on central field manipulation device 100. As another non-limiting example, a first magnetic field of recess 308 may include a south pole, and a second end of recess 308 may include a north pole. Central field manipulation device 100 may align a south pole with a north pole of recess 308, causing an attracting force on central field manipulation device 100. One or more bar magnets may be configured to keep central field manipulation device 100 in a stationary position. In some embodiments, central field manipulation device 100 may be moved from a stationary position, which may cause an oscillation of central field manipulation device 100 as one or more bar magnets of interconnecting component 304 pull central field manipulation device 100 back to a stationary and/or origin point. In some embodiments, interconnecting component 304 may include one or more bar magnets that may be placed underneath recess 308. Central field manipulation device 100 may be configured to bounce back and forth between two ends of recess 308. A user may "flick" or otherwise push central field manipulation device 100 in a direction of recess 308, which may cause an oscillating movement of central field manipulation device 100. A movement of central field manipulation device 100 between two ends of recess 308 may act as a fidgeting device, in which a neurodivergent user may increase focus and concentration when engaging with apparatus 300.

Still referring to FIG. 3, in some embodiments, interconnecting component 304 may include a field generating component on a bottom side. A field generating component on a bottom side of interconnecting component 304 may be configured to pull central field manipulation device to the bottom side of interconnecting component 304. A user may shake or otherwise vibrate interconnecting component 304 in an attempt to shake off central field manipulation device 100 from interconnecting component 304. In some embodiments, interconnecting component 304 may include a spring device. A spring device may be positioned on an end of interconnecting component 304. A spring device may be configured to be pressed down by a user and upon release may be configured to apply a force to central field manipulation device 100. As such, interconnecting component 304 may include two or more modes of operation.

Figure 4:
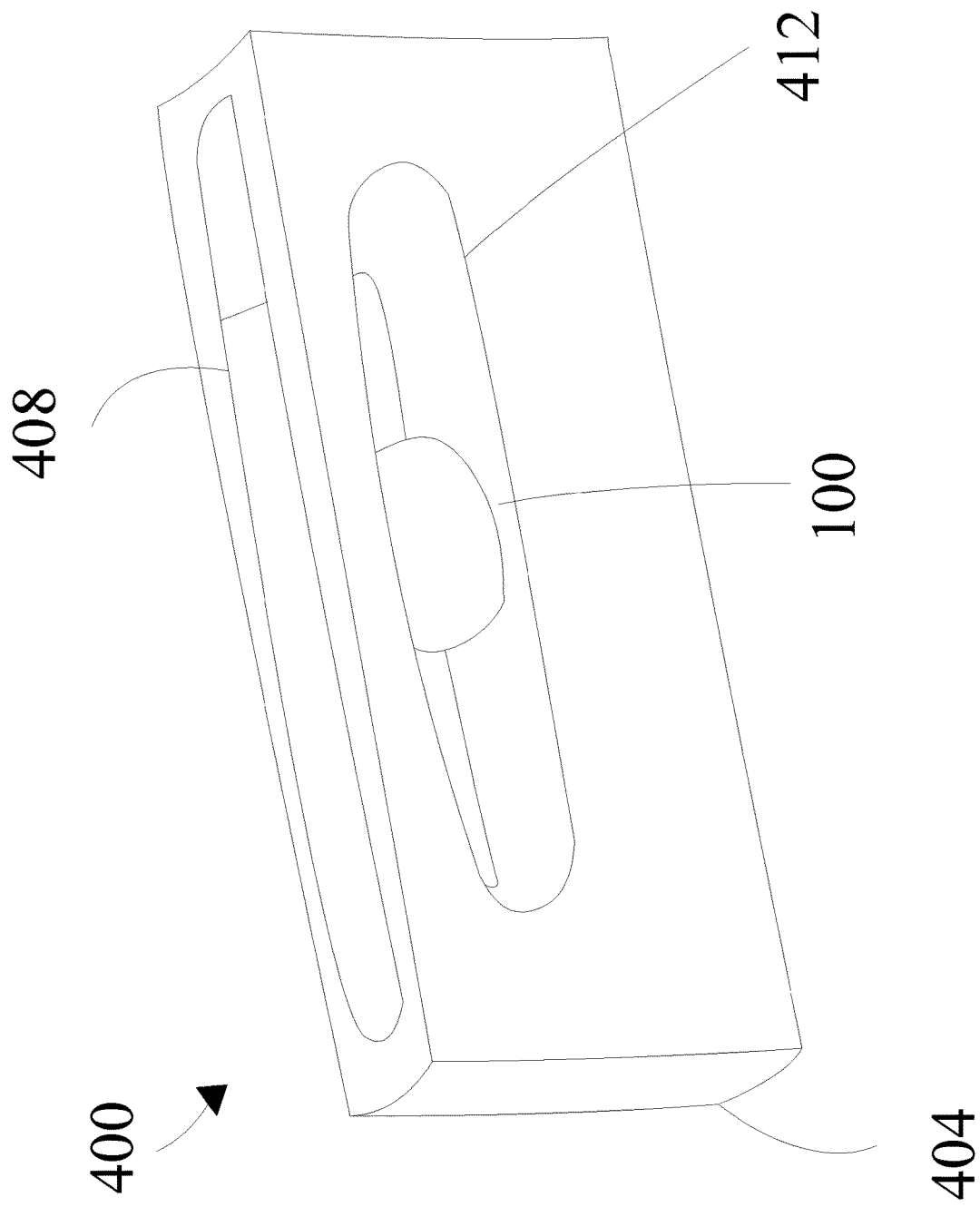
FIG. 4 is another exemplary embodiment of a modular field manipulation apparatus showing a housing.

Now referring to FIG. 4, an exemplary embodiment of a modular field manipulation apparatus 400 is shown. Apparatus 400 may include interconnecting component 404. Interconnecting component 404 may include a rigid material such as, but not limited to, wood, plastic, and the like. In some embodiments, interconnecting component 404 may include a shape, such as, but not limited to, a rectangle, square, and the like. Interconnecting component 404 may include slot 408. Slot 408 may be configured to receive central field manipulation device 100. Central field manipulation device 100 may be positioned into recess 412 through slot 408. In some embodiments, recess 412 may be configured to oscillate central field manipulation device 100 through opposing magnetic fields, similarly described above in FIG. 3.

Still referring to FIG. 4, slot 408 may be configured to receive a finger of a user. A user may place a finger into slot 408 to "flick" or otherwise push central field manipulation device 100 towards an end of recess 412, which may cause an oscillating movement. In some embodiments, central field manipulation device 100 may begin an oscillating movement through a user applied movement of interconnecting component 404. As a non-limiting example, a user may hold interconnecting component 404 in its entirety and shake interconnecting component 404. A shaking of interconnecting component 404 may cause an oscillating movement of central field manipulation device 100. In some embodiments, interconnecting component 404 may include a viewpoint of recess 412. A viewpoint of recess 412 may be configured to show a user a movement of central field manipulation device 100. In some embodiments, apparatus 400 may include a cover for interconnecting component 404. A cover of interconnecting component 404 may be applied on slot 408, which may prevent central field manipulation device 100 from falling out of interconnecting component 404. In some embodiments, interconnecting component 404 may include a field generating component of an opposite polarity of central field manipulation device 100 on a bottom portion of interconnecting component 404, which may act as a holder for central field manipulation device 100. In some embodiments, interconnecting component 404 may include a weighted element. A "weighted element" as used in this disclosure is any object that gives more mass to another object. In some embodiments, a weighted element may be positioned inside interconnecting component 404. A weighted element may be configured to oscillate inside interconnecting component 404, which may induce more muscle activity in a user engaging with apparatus 400. In some embodiments, interconnecting component 404 may include one or more housing components for one or more weighted elements. A user may select a weighted element and place the weighted element in a housing component.

Figure 5:
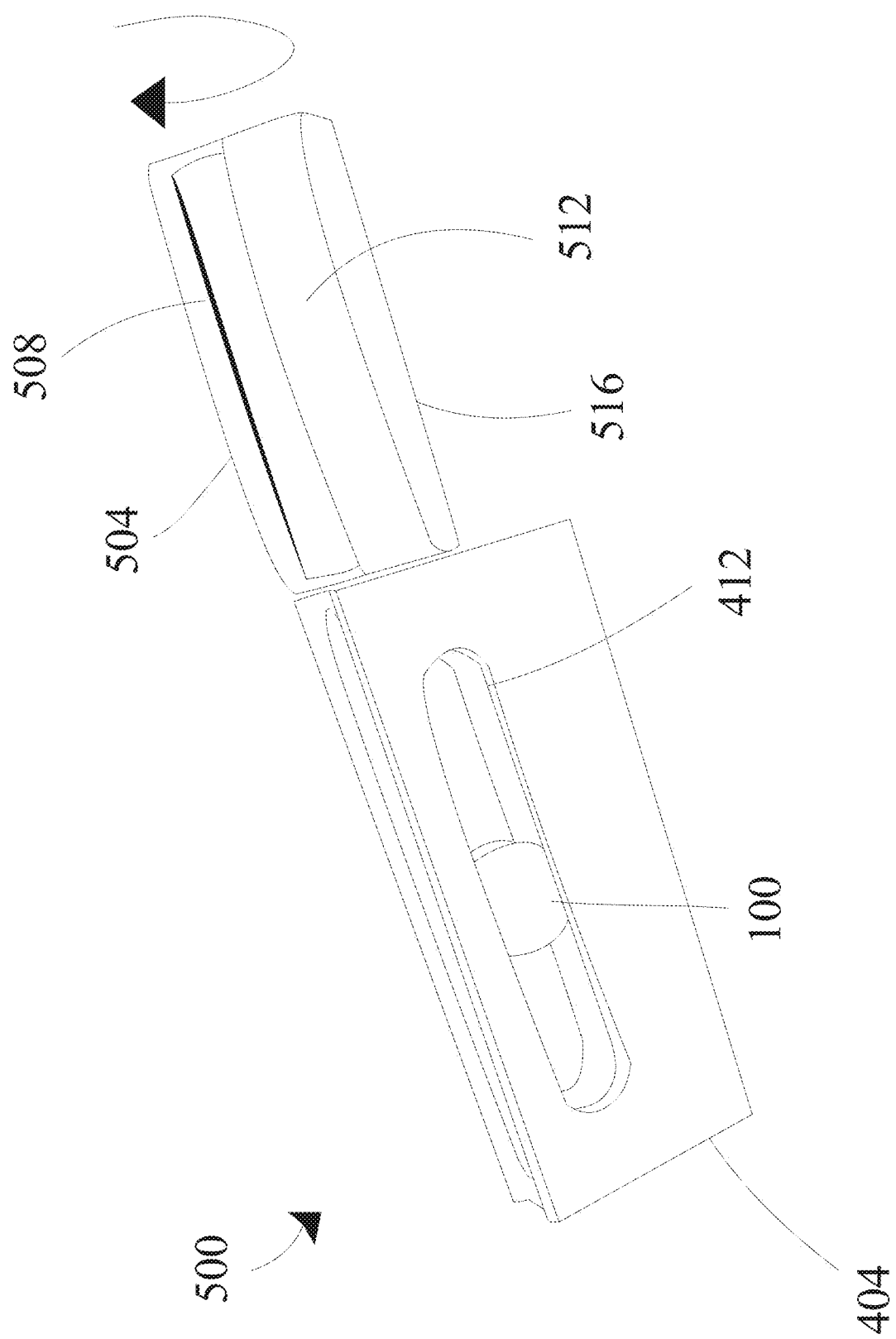
FIG. 5 is another exemplary embodiment of a modular field manipulation apparatus showing a field modifier.

Now referring to FIG. 5, another exemplary embodiment of a modular field manipulation apparatus 500 is shown. Apparatus 500 may include interconnecting component 404 as described above with reference to FIG. 4. Apparatus 500 may include field modifier 504. Field modifier 504 may include one or more field generating components. Field modifier 504 may include top portion 508. Top portion 508 may include grasping element 512. Grasping element 512 may include, but is not limited to, a strut, bearing, protrusion and the like. Grasping element 512 may include grasping elements as described above. Field modifier 504 may include bottom portion 516. Bottom portion 516 may include a grasping element. Field modifier 504 may include a color code. A color code may include one or more colors corresponding to one or more field polarities. A color code may include red, green, blue, and/or any combination thereof. In some embodiments, a color code may include a color denoting a negative field polarity, such as black and/or purple. In some embodiments, a color code may include a color denoting a positive field polarity, such as white and/or yellow. Top portion 508 may include a first color identifying top portion 508 and/or bottom portion 516 may include a second color identifying bottom portion 516. In some embodiments, field modifier 504 may be configured to be positioned near an end of interconnecting component 404. In some embodiments, field modifier 504 may attract central field manipulation device 100 through a magnetic field interaction. Central field manipulation device 100 may stick to an end of recess 412 through a field interaction with field modifier 504. In some embodiments, field modifier 504 may be configured to rotate about a rotation axis. A "rotation axis" as used in this disclosure is an axis about which an object rotates. In some embodiments, field modifier 504 may be configured to rotate about an x-axis in a clockwise and/or counterclockwise direction. A rotation of field modifier 504 may cause a changing magnetic attraction between field modifier 504 and central field manipulation device 100. As a non-limiting example, field modifier 504 may be turned clockwise, which may oppose a field of central field manipulation device 100, pushing it to an opposing side of recess 412. In another non-limiting example, a counterclockwise rotation of field modifier 504 may attract a magnetic field of central field manipulation device 100. A user may engage with apparatus 500 to oscillate central field manipulation device 100 back and forth in recess 412 of interconnecting component 404 through a rotation of field modifier 504.

Figure 6:
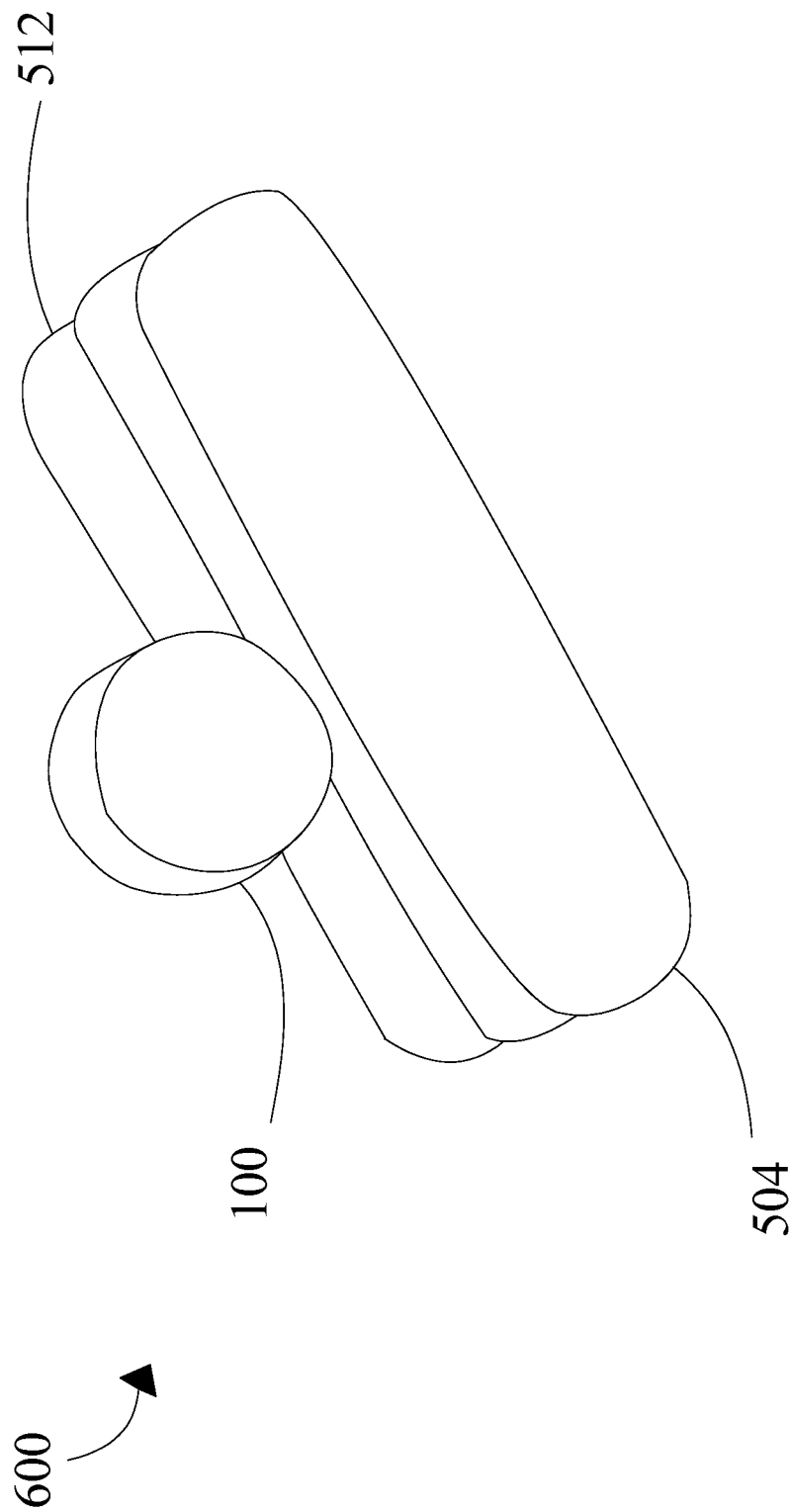
FIG. 6 is another exemplary embodiment of a modular field manipulation apparatus with a field modifier.

Now referring to FIG. 6, another exemplary embodiment of a modular field manipulation apparatus 600 is shown. Apparatus 600 may include field modifier 504. Field modifier 504 may include a magnetic field that may surround an exterior portion of field modifier 504. A magnetic field of field modifier 504 may attract a magnetic field of central field manipulation device 100. In some embodiments, field modifier 504 may be configured to direct a movement of central field manipulation device 100 around a perimeter of field modifier 504. In some embodiments, central field manipulation device 100 may be configured to travel along a perimeter of field modifier 504 in a clockwise and/or counterclockwise direction. In some embodiments, a user may "flick" or otherwise push central field manipulation device 100, which may cause central field manipulation device 100 to travel clockwise and/or counterclockwise around a perimeter of field modifier 504.

Figure 7:
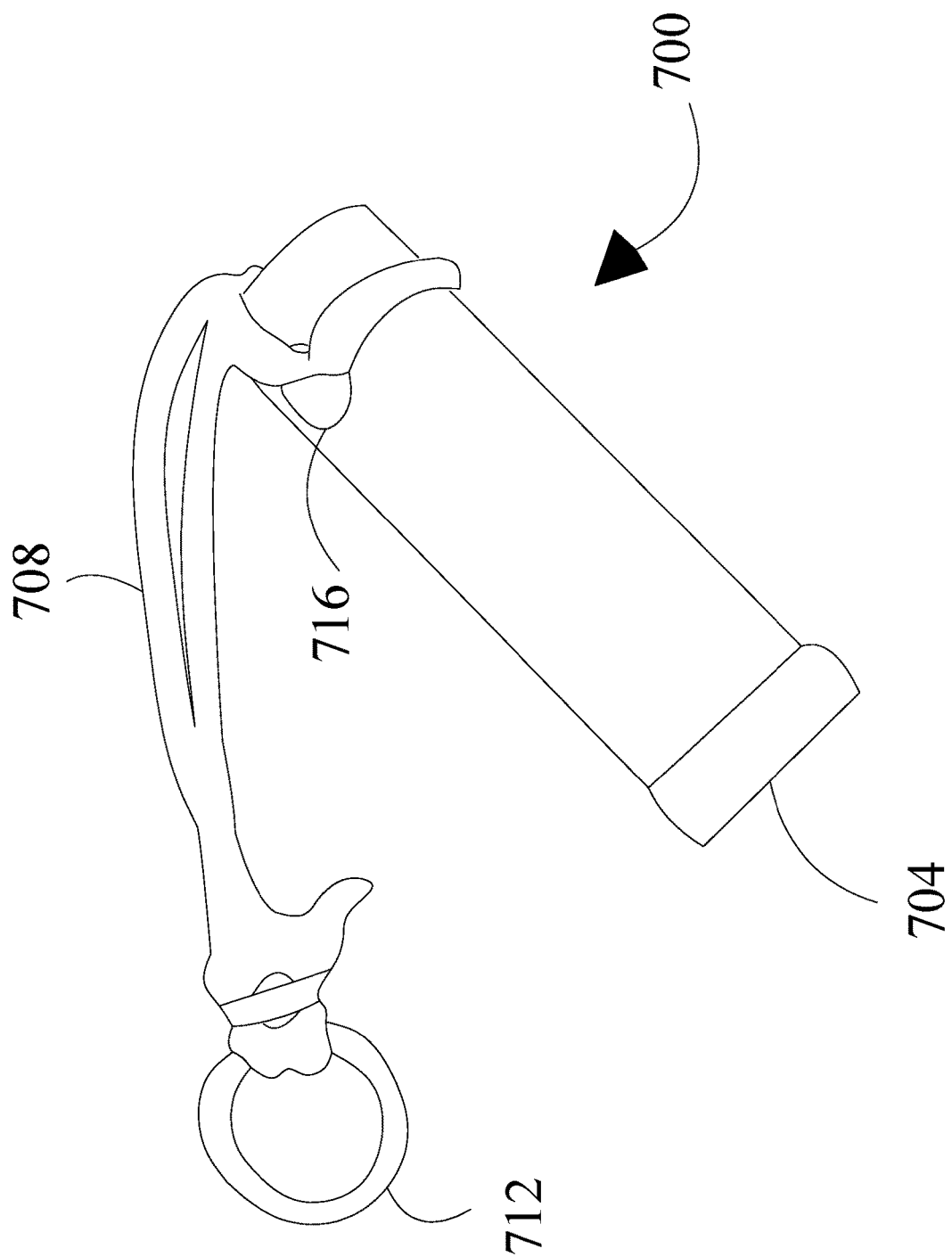
FIG. 7 is another exemplary embodiment of a modular field manipulation apparatus showing a tether configuration.

Now referring to FIG. 7, another exemplary embodiment of a modular field manipulation apparatus 700 is shown. Apparatus 700 may include interconnecting component 704. Interconnecting component 704 may include a shape, such as, but not limited to, a cylinder, rectangle, square, and the like. Interconnecting component 704 may include a rigid material such as, but not limited to, wood, plastic, and the like. Interconnecting component 704 may include a field manipulation device which may be configured to hold central field manipulation device 100 in place. In some embodiments, interconnecting component 704 may include tether 708. A "tether" as used in this disclosure is any component configured to apply tension to two or more objects. Tether 708 may include, but is not limited to, a rope material, rubber material, and the like. Tether 708 may be wrapped through tether slot 716. Tether slot 716 may include a hole through interconnecting component 704 that may allow a passage of tether 708. In some embodiments, tether 708 may be configured to attach loop 712 to interconnecting component 704. Loop 712 may include a magnetic material that may be configured to attract a magnetic field of central field manipulation device 100. In some embodiments, interconnecting component 704 may include an indentation at a top surface. An indentation at a top surface may be configured to hold central field manipulation device 100. In some embodiments, a user may grasp interconnecting component 704 along and apply a force to tether 708 which may pull loop 712 to a top surface of interconnecting component 704. Loop 712 may attach to central field manipulation device 100 at a top surface of interconnecting component 704. A user may engage with apparatus 700 in a "ball and cup" manner.

Figure 8:
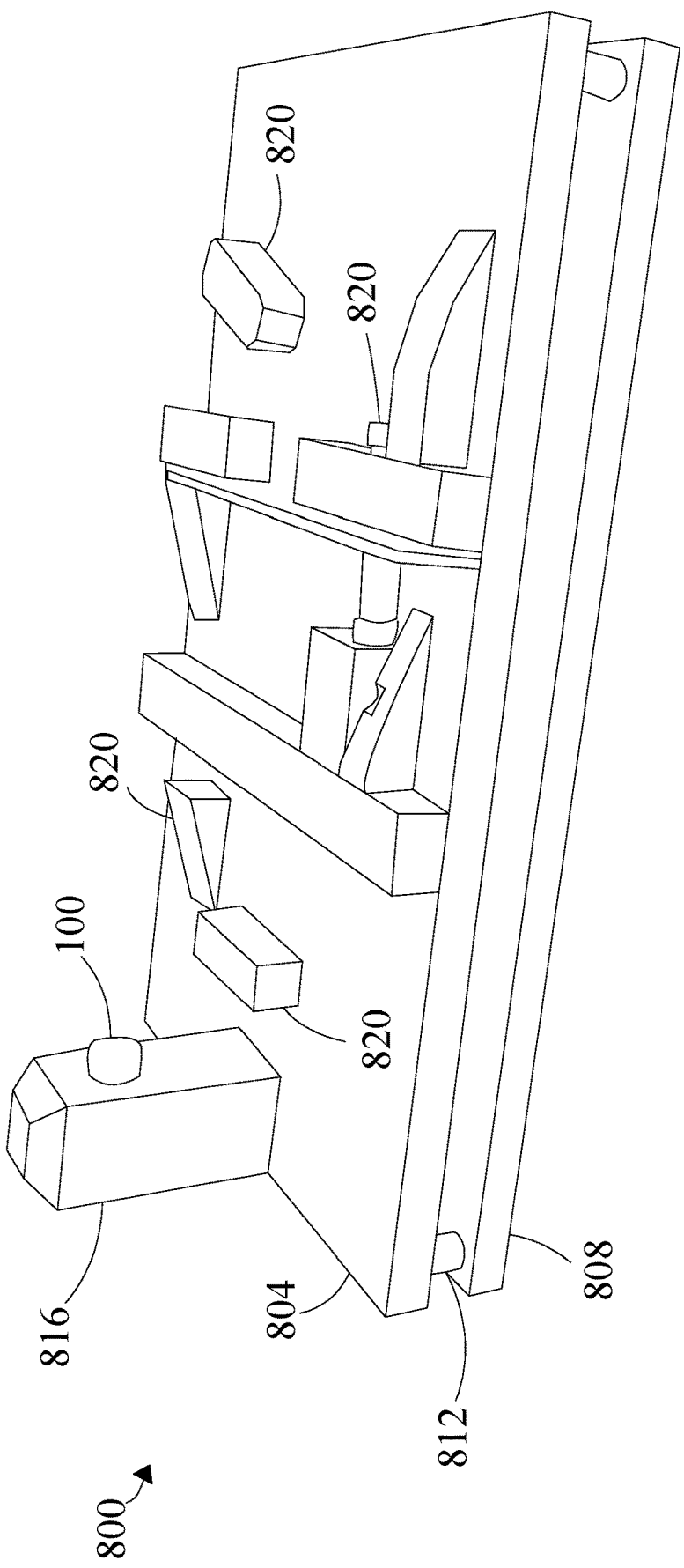
FIG. 8 is another exemplary embodiment of a modular field manipulation apparatus showing an obstacle course.

Now referring to FIG. 8, another exemplary embodiment of a modular field manipulation apparatus 800 is presented. Apparatus 800 may include table 804. Table 804 may include a shape, such as, but not limited to, a rectangle, square, and the like. In some embodiments, table 804 may include a rigid material such as, but not limited to, wood, plastic, and the like. Table 804 may be supported on bottom side 808 through supporting structure 812. Bottom side 808 may include an identical structure to table 804. In other embodiments, bottom side 808 may include varying dimensions from table 804. Supporting structures 812 may include a cylindrical shape that may allow for an open space between table 804 and bottom side 808. An open space between table 804 and bottom side 808 may allow for a field manipulation device to pass underneath obstacles 820 of table 804. Apparatus 800 may be configured to provide an obstacle course for a user to manipulate central field manipulation device 100 through. Obstacles 820 may include a variety of shapes, sizes, and the like. In some embodiments, obstacles 820 may include a sloped structure. In other embodiments, obstacles 820 may include a rectangular, rhomboid, and/or other structure. In some embodiments, obstacles 820 may include a tube structure that may allow a passage of central field manipulation device 100. Obstacles 820 may be configured to apply physical force against a movement of central field manipulation device 100. Obstacles 820 may include magnetic materials which may oppose a magnetic field of central field manipulation device 100. In other embodiments, obstacles 820 may include non-magnetic materials, such as wood. Obstacles 820 may include a revolving structure, such as a revolving door. Obstacles 820 may include a draw bride having a counterweight. A counterweight may be configured to open and/or close a draw bridge of obstacles 820. Apparatus 800 may include tower 816. Tower 816 may act as a "finishing line" for central field manipulation device 100. A user may start an obstacle course on a side of table 804 opposite that of tower 816. A user may maneuver central field manipulation device 100 through obstacles 820 to reach tower 816. In some embodiments, apparatus 800 may be configured to include one or more paths for a user to manipulate central field manipulation device 100 through. As a non-limiting example, a first path may include an obstacle 820 in a form of a wall. A user may traverse a wall by manipulating central field manipulation device 100 through gaps between stationary blocks and moveable obstacles, where the moveable obstacles may be shaped to fit between the gaps of the stationary blocks, which may create a bridge-like structure to go over the wall. Continuing this example, a user may intuitively create a bridge-like structure or alternatively traverse the wall by manipulating moving obstacles in a different way, such as stacking them. Tower 816 may include a magnetic field which may act as a holder for central field manipulation device 100.

Figure 9:
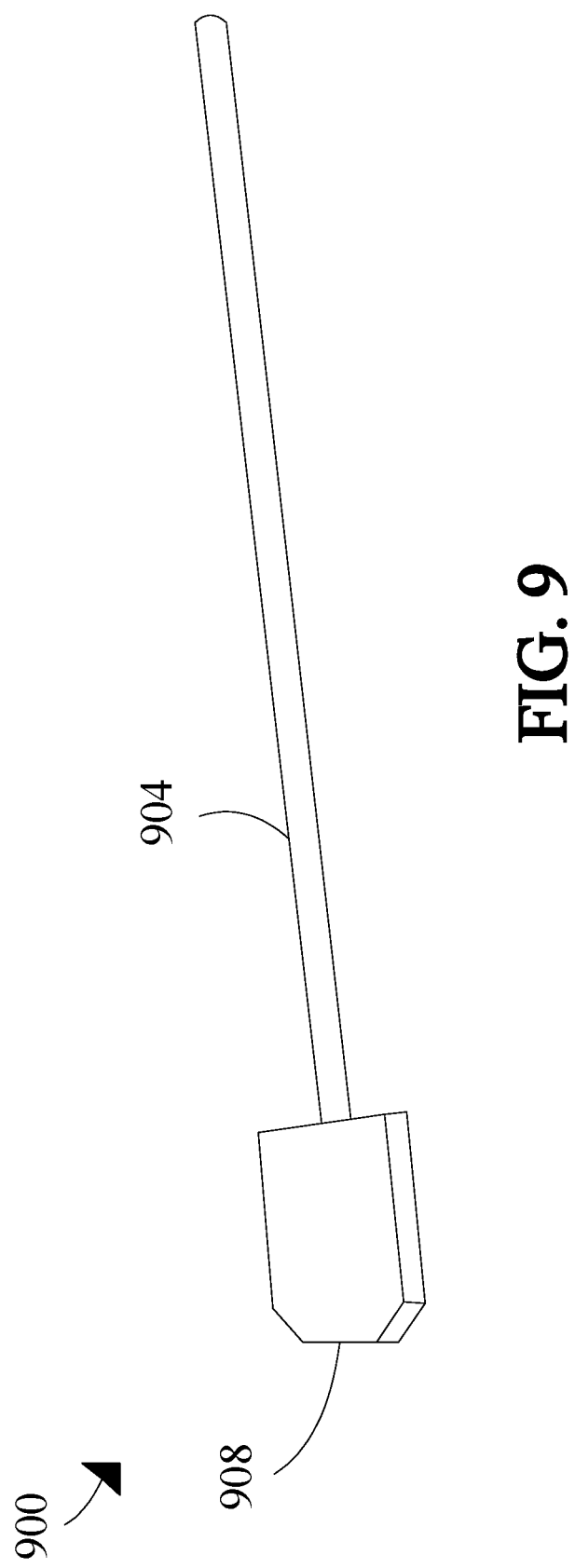
FIG. 9 is an exemplary embodiment of a field manipulation tool.

Now referring to FIG. 9, an exemplary embodiment of a central field manipulation device 900 is presented. Central field manipulation device 900 may include a handle 904. A handle 904 may include a shape such as, but not limited to, a cylinder, rectangle, and the like. Handle 904 may include a gripping element for a user to grasp. In some embodiments, device 900 may include director 908. Director 908 may include a magnetic surface that may be configured to interact with a magnetic field of central field manipulation device 100 through table 804. Director 908 may include a shape such as, but not limited to, a rectangle, circle, rhombus, polygons, and the like. In some embodiments, device 900 may be used with apparatus 800 to maneuver central field manipulation device 100 through obstacles 820. Handle 904 of device 900 may include a length that may allow a user to cover every area of table 804.

Figure 10:
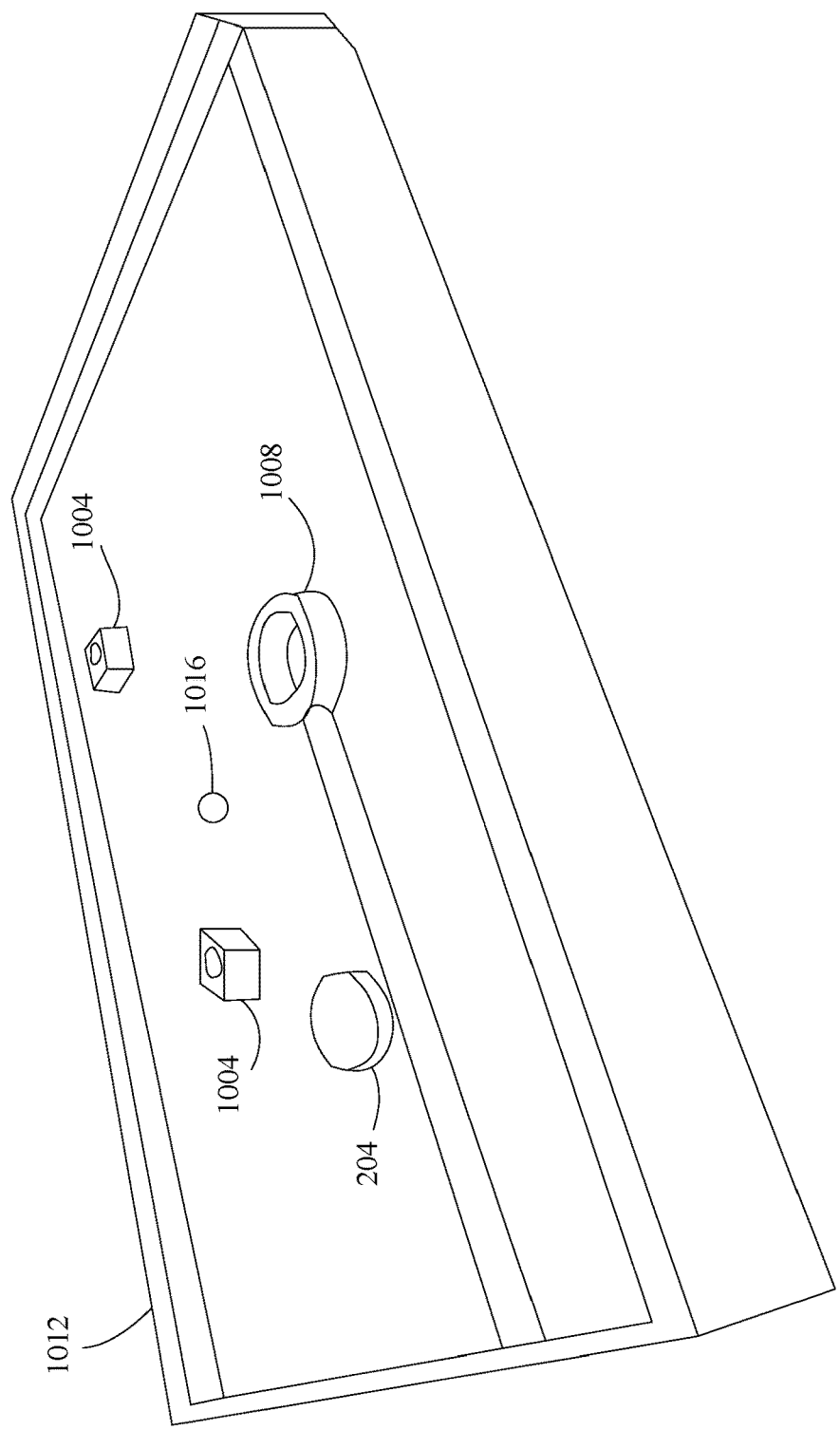
FIG. 10 is another exemplary embodiment of a modular field manipulation apparatus.

Now referring to FIG. 10, another exemplary embodiment of a modular field manipulation apparatus 1000 is shown. Apparatus 1000 may include a shape such as, but not limited to, rectangular, square, ovular, and the like. In some embodiments, central field manipulation device 100 may be placed in holders 1004. Holders 1004 may include a square shape. In some embodiments, holder 1004 may include a magnetic material that may attract a magnetic field of central field manipulation device 100. In some embodiments, central field manipulation device 100 may be placed in a first holder, and a second central field manipulation device may be placed in a second holder. Apparatus 1000 may include tool 1008. Tool 1008 may include a handle and magnetic material as described above with reference to FIG. 9. Tool 1008 may be configured to hold interconnecting component 204. A user may place tool 1008 with interconnecting component 204 underneath table 1012. A user may manipulate holder 1004 which may hold central field manipulation device 100 through tool 1008. In some embodiments, a second user may use a second tool to move a second holder through magnetic field manipulation. Two or more user may use a maneuvering of holders 1004 to direct a movement of moving piece 1016. Moving piece 1016 may include a non-magnetic material such as, but not limited to, plastic, wood, and the like. Moving piece 1016 may include a shape such as, but not limited to, balls, pucks, diamonds, triangles, squares, ovals, and the like. Two or more users may enter a contention in which a victor may be determined by a first user directing moving piece 1016 to a second user's side. In some embodiments, table 1012 of apparatus 1000 may include one or more moving piece slots. A moving piece slot may include an opening in table 1012 that may allow a passage of moving piece 1016. In some embodiments, table 1012 may include pictograms, colors, and other visual aids for a user to direct moving piece 1016 through.

Figure 11:
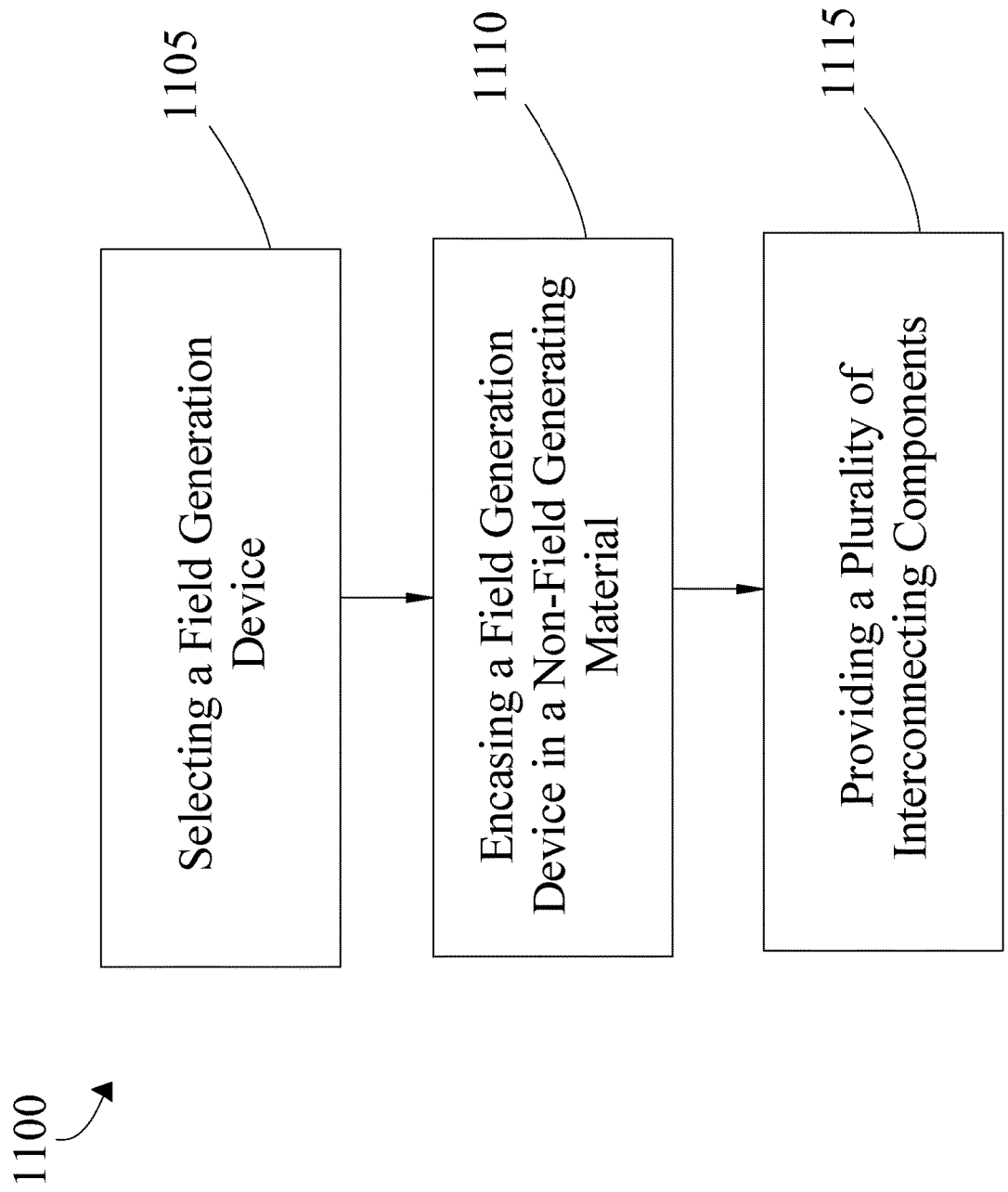
FIG. 11 is an exemplary embodiment of a method of manufacturing a central field manipulation device.

Now referring to FIG. 11, method of manufacturing a modular field manipulation apparatus is presented. Manufacturing and/or forming of a part, workpiece, or other object may be performed, without limitation, using a manufacturing device. A manufacturing device may include an additive manufacturing device. An additive manufacturing device may include without limitation any device designed or configured to produce a component, product, or the like using an additive manufacturing process, in which material is deposited on the workpiece to be turned into the finished result. In some embodiments, an additive manufacturing process is a process in which material is added incrementally to a body of material in a series of two or more successive steps. The material may be added in the form of a stack of incremental layers; each layer may represent a cross-section of the object to be formed upon completion of the additive manufacturing process. Each cross-section may, as a non-limiting example be modeled on a computing device as a cross-section of graphical representation of the object to be formed; for instance, a computer aided design (CAD) tool may be used to receive or generate a three-dimensional model of the object to be formed, and a computerized process may derive from that model a series of cross-sectional layers that, when deposited during the additive manufacturing process, together will form the object. The steps performed by an additive manufacturing system to deposit each layer may be guided by a computer aided manufacturing (CAM) tool. In other embodiments, a series of layers are deposited in a substantially radial form, for instance by adding a succession of coatings to the workpiece. Similarly, the material may be added in volumetric increments other than layers, such as by depositing physical voxels in rectilinear or other forms. Additive manufacturing, as used in this disclosure, may specifically include manufacturing done at the atomic and nano level. Additive manufacturing also includes bodies of material that are a hybrid of other types of manufacturing processes, e.g. forging and additive manufacturing as described above. As an example, a forged body of material may have welded material deposited upon it which then comprises an additive manufactured body of material.

Still referring to FIG. 11, deposition of material in additive manufacturing processes may be accomplished by any suitable means. Deposition may be accomplished using stereolithography, in which successive layers of polymer material are deposited and then caused to bind with previous layers using a curing process such as curing using ultraviolet light. Additive manufacturing processes may include "three-dimensional printing" processes that deposit successive layers of power and binder; the powder may include polymer or ceramic powder, and the binder may cause the powder to adhere, fuse, or otherwise join into a layer of material making up the body of material or product. Additive manufacturing may include metal three-dimensional printing techniques such as laser sintering including direct metal laser sintering (DMLS) or laser powder-bed fusion. Likewise, additive manufacturing may be accomplished by immersion in a solution that deposits layers of material on the body of material, by depositing and sintering materials having melting points such as metals, such as selective laser sintering, by applying fluid or paste-like materials in strips or sheets and then curing that material either by cooling, ultraviolet curing, and the like, any combination of the above methods, or any additional methods that involve depositing successive layers or other increments of material. Methods of additive manufacturing may include without limitation vat polymerization, material jetting, binder jetting, material extrusion, fuse deposition modeling, powder bed fusion, sheet lamination, and directed energy deposition. Methods of additive manufacturing may include adding material in increments of individual atoms, molecules, or other particles. An additive manufacturing process may use a single method of additive manufacturing, or combine two or more methods.

Still referring to FIG. 11, additive manufacturing may include deposition of initial layers on a substrate. Substrate may include, without limitation, a support surface of an additive manufacturing device, or a removable item placed thereon. Substrate may include a base plate, which may be constructed of any suitable material; in some embodiments, where metal additive manufacturing is used, base plate may be constructed of metal, such as titanium. Base plate may be removable. One or more support features may also be used to support additively manufactured body of material during additive manufacture; for instance and without limitation, where a downward-facing surface of additively manufactured body of material is constructed having less than a threshold angle of steepness, support structures may be necessary to support the downward-facing surface; threshold angle may be, for instance 45 degrees. Support structures may be additively constructed, and may be supported on support surface and/or on upward-facing surfaces of additively manufactured body of material. Support structures may have any suitable form, including struts, buttresses, mesh, honeycomb or the like; persons skilled in the art, upon reviewing the entirety of this disclosure, will be aware of various forms that support structures may take consistently with the described methods and systems.

Still referring to FIG. 11, an additive manufacturing device may include an applicator or other additive device. For instance, an additive manufacturing device may include a printer head for a 3D printer. An additive manufacturing device may include an extruding device for extruding fluid or paste material, a sprayer or other applicator for bonding material, an applicator for powering, a sintering device such as a laser, or other such material.

Still referring to FIG. 11, an additive manufacturing device may include one or more robotic elements, including without limitation robot arms for moving, rotating, or otherwise positioning a workpiece, or for positioning a manufacturing tool, printer heads, or the like to work on workpiece. An additive manufacturing device may include one or more workpiece transport elements for moving a workpiece or finished part or component from one manufacturing stage to another; workpiece transport elements may include conveyors such as screw conveyors or conveyor belts, hoppers, rollers, or other items for moving an object from one place to another.

Still referring to FIG. 11, a manufacturing device may include a subtractive manufacturing device, which may perform one or more subtractive manufacturing processes. One or more steps may include a subtractive manufacturing process, which produces the product by removing material from a workpiece; the removal of material may be accomplished using abrasives, cutting tools or endmills, laser cutting or ablation, removal using heat, or any other method that removes material from the workpiece. Each subtractive manufacturing process used may be any suitable process, such as, but not limited to, rotary-tool milling, electronic discharge machining, ablation, etching, erosion, cutting, sawing, sanding, polishing, grinding, and cleaving, among others.

Still referring to FIG. 11, if rotary-tool milling is utilized, this milling may be accomplished using any suitable type of milling equipment, such as milling equipment having either a vertically or horizontally oriented spindle shaft. Examples of milling equipment include bed mills, turret mills, C-frame mills, floor mills, gantry mills, knee mills, and ram-type mills, among others. In some embodiments, the milling equipment used for removing material may be of the computerized numerical control (CNC) type that is automated and operates by precisely programmed commands that control movement of one or more parts of the equipment to effect the material removal. CNC machines, their operation, programming, and relation to CAM tools and CAD tools are well known and need not be described in detail herein for those skilled in the art to understand the scope of the present invention and how to practice it in any of its widely varying forms.

Still referring to FIG. 11, subtractive manufacturing may be performed using spark-erosive devices; for instance, subtractive manufacturing may include removal of material using electronic discharge machining (EDM). EDM may include wire EDM, plunge EDM, immersive EDM, ram EDM, or any other EDM manufacturing technique. Subtractive manufacturing may be performed using laser-cutting processes. Subtractive manufacturing may be performed using water-jet or other fluid-jet cutting techniques. Fundamentally, any process for removal of material may be employed for subtractive manufacturing.

With continued reference to FIG. 11, a manufacturing device may include a mechanical manufacturing device. In an embodiment, a mechanical manufacturing device may be a manufacturing device that deprives the user of some direct control over the toolpath, defined as movements the manufacturing tool and workpiece make relative to one another during the one or more manufacturing steps. For instance, a manufacturing tool may be constrained to move vertically, by a linear slide or similar device, so that the only decision the user may make is to raise or lower the manufacturing tool; as a non-limiting example, where a manufacturing device is a manually operated machine tool, user may only be able to raise and lower a cutting tool, and have no ability to move the cutting tool horizontally. Similarly, where a manufacturing tool includes a slide lathe, a blade on the slide lathe may be constrained to follow a particular path. As a further example, a base table may be moveable along one or more linear axes; for instance, a base table may be constrained to move along a single horizontal axis. In other embodiments, a base table is constrained to movement along two horizontal axes that span two dimensions, permitting freedom of movement only in a horizontal plane; for instance, a base table may be mounted on two mutually orthogonal linear slides.

Still referring to FIG. 11, a manufacturing device may include a powered manufacturing device. In an embodiment, a powered manufacturing device may be a manufacturing device in which at least one component of the manufacturing device includes at least a component powered by something other than human power. At least a component may be powered by any non-human source, including without limitation electric power generated or stored by any means, heat engines including steam, internal combustion, or diesel engines, wind power, water power, pneumatic power, or hydraulic power. Powered components may include any components of manufacturing device. A manufacturing tool may be powered; for instance, a manufacturing tool may include an endmill mounted on a spindle rotated by a motor (not shown). A workpiece support may be powered. Where a manufacturing device is a mechanical device, motion of components along linear or rotary constraints may be powered; for instance, motion of a base table along one or more linear constraints such as linear slides may be driven by a motor or other source of power. Similarly, rotation of a table may be driven by a power source. A tool-changer, where present, may be driven by power. In some embodiments, all or substantially all of the components of a manufacturing device are powered by something other than human power; for instance, all components may be powered by electrical power.

Still referring to FIG. 11, a manufacturing device may include an automated manufacturing system. In some embodiments, an automated manufacturing system is a manufacturing device including a controller that controls one or more manufacturing steps automatically. A controller may include a sequential control device that produces a sequence of commands without feedback from other components of automated manufacturing system. A controller may include a feedback control device that produces commands triggered or modified by feedback from other components. A controller may perform both sequential and feedback control. In some embodiments, a controller includes a mechanical device. In other embodiments, a controller includes an electronic device. An electronic device may include digital or analog electronic components, including without limitation one or more logic circuits, such one or more logic gates, programmable elements such as field-programmable arrays, multiplexors, one or more operational amplifiers, one or more diodes, one or more transistors, one or more comparators, and one or more integrators. An electronic device may include a processor. An electronic device may include a computing device. A computing device may include any computing device as described below. A computing device may include a computing device embedded in manufacturing device; as a non-limiting example, computing device may include a microcontroller, which may be housed in a unit that combines the other components of manufacturing device. A controller may include a manufacturer client of plurality of manufacturer clients; controller may be communicatively coupled to a manufacturer client of plurality of manufacturer clients.

Still referring to FIG. 11, a controller may include a component embedded in manufacturing device; as a non-limiting example, a controller may include a microcontroller, which may be housed in a unit that combines the other components of a manufacturing device. Further continuing the example, a microcontroller may have program memory, which may enable a microcontroller to load a program that directs a manufacturing device to perform an automated manufacturing process. Similarly, a controller may include any other components of a computing device as described below in a device housed within a manufacturing device. In other embodiments, a controller includes a computing device that is separate from the rest of the components of a manufacturing device; for instance, a controller may include a personal computer, laptop, or workstation connected to the remainder of a manufacturing device by a wired or wireless data connection. In some embodiments, a controller includes both a personal computing device where a user may enter instructions to generate a program for turning a workpiece into a finished product, and an embedded device that receives the program from the personal computing device and executes the program. Persons skilled in the art will be aware of various ways that a controller, which may include one or more computing devices, may be connected to or incorporated in an automated manufacturing system as described above.

Still referring to FIG. 11, a controller may control components of automated manufacturing system; for instance, a controller may control elements including without limitation tool changer to switch endmills, spindle or gear systems operatively coupled to spindle to regulate spindle rotational speed, linear movement of manufacturing tool, base table, or both, and rotation or rotational position of rotary table. As a non-limiting example, a controller may coordinate deposition and/or curing of a material in an additive manufacturing processes, where a manufacturing device is an additive manufacturing device. Persons skilled in the art, upon reading the entirety of this disclosure, will be aware of similar automated control systems usable for various forms manufacturing.

Still referring to FIG. 11, a controller may be designed and/or configured to perform any method, method step, or sequence of method steps in any embodiment described in this disclosure, in any order and with any degree of repetition. For instance, a controller may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A controller may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 11, an object, part, and/or workpiece may be further processed as desired to finish that object, part, and/or workpieces. Examples of further process include but are not limited to: secondary machining, polishing, coating such as powder coating, anodization, silk-screening, and any combination thereof, among others. Fundamentally, there is no limitation on the finishing steps, if any, that may occur for a finishing step.

Still referring to FIG. 11, at step 1105, method 1100 includes selecting a field generation device. A field generating device may include, but is not limited to, bar magnets, circular magnets, square magnets, and the like. A field generation device may be selected based on size, shape, field strength, and the like. In some embodiments, a field generating device may include a plurality of magnets. A plurality of magnets of a field generation device may be positioned next to and/or on top of each other. In some embodiments, a plurality of magnets may be stacked on top one another. A plurality of magnets may be oriented to align polarities of magnetic fields of each magnet. In some embodiments, each magnetic field of a plurality of magnets may be aligned such that a top of a stack of a plurality of magnets has a first polarity and a bottom of the stack of the plurality of magnets has a second polarity. A plurality of magnets may be held in place with an adhesive. In some embodiments, a field generation device may be manufactured. For instance and without limitation, a field generation device may be carved out of a larger slab of a field generation material. In some embodiments, a field generation device may be manufactured through powder metallurgy. Power metallurgy may include pulverizing a suitable composition into fine powder, which may be compacted and heated to cause densification through liquid phase sintering. In other embodiments, a field generation device may be manufactured through apply a magnetic field to a ferromagnetic material. In some embodiments, a field generation device may be produced through any manufacturing method as described above. A field generation device may be pre-fabricated, and selected based on a variety of factors as described above.

Still referring to FIG. 11, at step 1110, method 1100 includes encasing a field generation device in a non-field generating material. A field generation device may be partially or fully encased in a non-field generating material. As a non-limiting example, a top and/or bottom portion of a field generating device may be encased in a non-field generating material, leaving side portions exposed. In some embodiments, a non-field generating material may be selected based on a variety of factors, such as, but not limited to, friction coefficients, rigidity, softness, field permeability, durability, and the like. In some embodiments, a non-field generating material may include, but is not limited to, wood, rubber, plastic, and the like. Encasing a central field generation device may produce a central field manipulation device. An encasement of a central field generation device may provide structural support to one or more magnets of the field generation device. In some embodiments, a field generation device may be housed within a casing of non-filed generating material. In some embodiments, a non-field generating material may be shaped or otherwise formed through additive or subtractive manufacturing. For instance, and without limitation, a non-field generating material may be cut from a larger slab of a non-field generating material to fit a surface area of a field generating device. In some embodiments, encasing a field generation device in a non-field generating material may include pouring a liquid material partially or fully around the field generation device. A liquid material may include, but is not limited to, epoxy. An epoxy may be cured, which may provide additional structural stability to a field generation device and/or an encasing of a field generation device. In some embodiments, producing a central field manipulation device may be performed by any manufacturing method as described above.

Still referring to FIG. 11, at step 1115, method 1100 includes providing a plurality of interconnecting components. A plurality of interconnecting components may be provided based on factors such as, but not limited to, shapes, materials, structures, sizes, and the like. A plurality of interconnecting components may include, but is not limited to including, wooden structures, metallic structures, rope structures, and the like. A plurality of interconnecting components may be manufactured through any manufacturing process as described above. In some embodiments, interconnecting components may be carved out of non-field generating materials as described above. In some embodiments, interconnecting components may be manufactured to have specific shapes, sizes, physical properties, and the like. For instance, and without limitation, an interconnecting component may be carved and/or shaped from a block of wood. An interconnecting component may be manufactured to have a cylindrical shape with holes at a top surface. Holes of an interconnecting component may be configured to allow a passage of rope, metallic hoops, and/or other structures. In some embodiments, one or more interconnecting components of a plurality of interconnecting components may be pre-fabricated. Providing a plurality of interconnecting components may include providing each interconnecting component with at least a contacting member. At least a contacting member may be configured to engage with at least a surface of a central field manipulation device. Providing each interconnecting component with at least a contacting member may include carving a portion out of an interconnecting component, where the carved portion acts as a contacting member. In other embodiments, at least a contacting member may be provided through an addition of a structure to an interconnecting component, such as, but not limited to, metallic rings, rope structures, and the like. At least a contacting member may be provided through any manufacturing process as described above.

Figure 12:
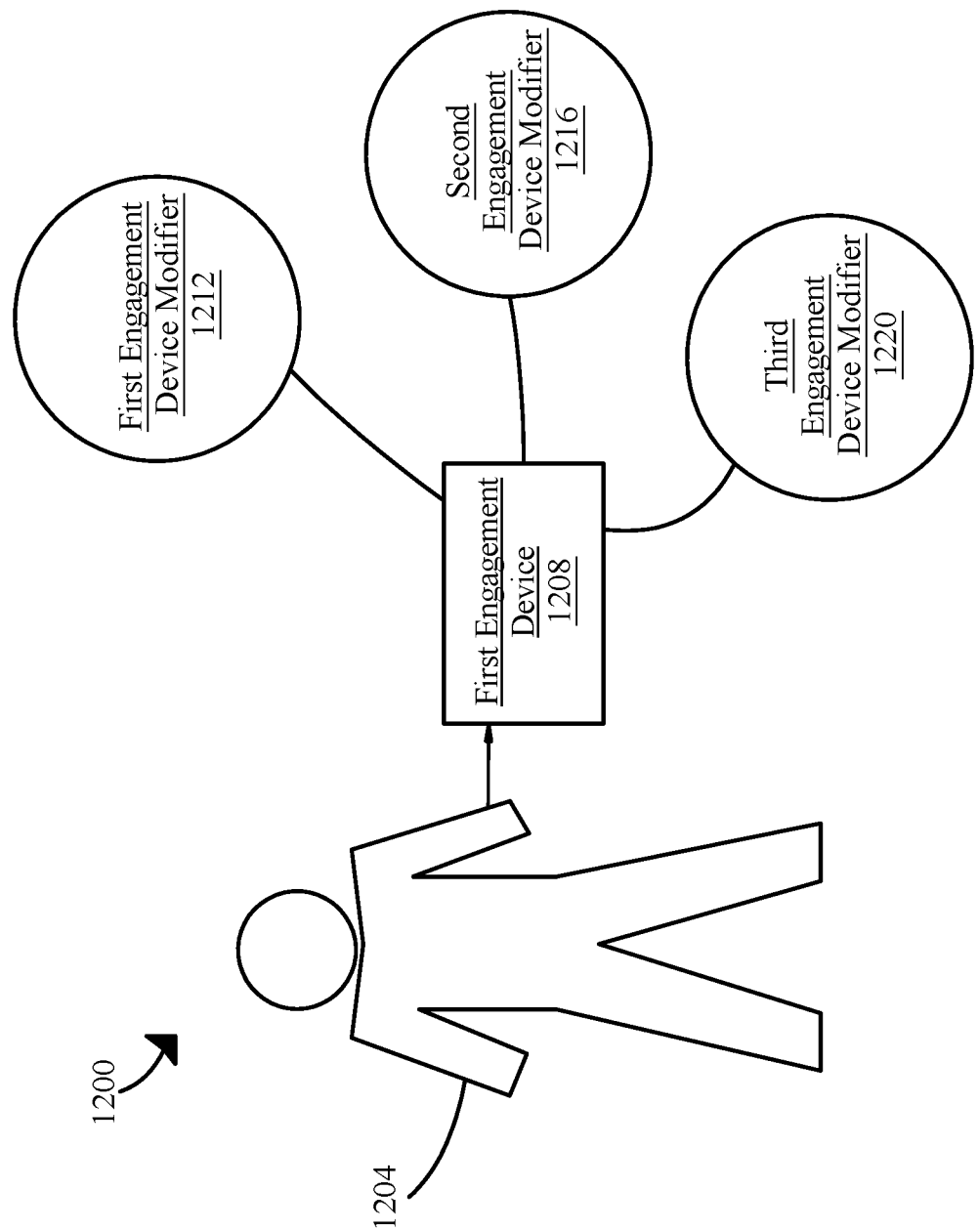
FIG. 12 is an exemplary embodiment of a system for cognitive skill development and coping strategies.

Now referring to FIG. 12, an exemplary embodiment of a system 1200 for cognitive skill development and coping strategies is illustrated. System 1200 may include entity 1204. An "entity" as used in this disclosure is any individual. In some embodiments, system 1200 may include two or more entities. Entity 1204 may include an entity with neurodivergent symptoms, such as, but not limited to, anxiety, restlessness, inability to focus, racing thoughts, irritability, and the like. Entity 1204 may engage with first engagement device 1208. First engagement device 1208 may include central field manipulation device 100, interconnecting component 204, and the like. Entity 1204 may engage with first engagement device 1208, which may reduce nervous energy of entity 1204. "Nervous energy" as used in this disclosure is any pent-up energy of an individual due to any neurodivergent ailment. In some embodiments, first engagement device 1208 may include a first surface having a first field polarity, such as central field manipulation device 100. In some embodiments, first engagement device 1208 may include a second surface which may be positioned opposite a first surface of first engagement device 1208. A second surface may include a second field polarity. First engagement device 1208 may interact with one or more engagement device modifiers through a first field polarity and/or a second field polarity. In some embodiments, first engagement device 1208 may include a grasping element. A grasping element may include, but is not limited to, a rough surface, indentures, recesses, and the like. In some embodiments, a first surface of first engagement device 1208 may include a grasping element. In some embodiments, a second surface of first engagement device 1208 may include a grasping element. First engagement device 1208 may include apparatus 200 as described above.

Still referring to FIG. 12, entity 1204 may become disinterested or disengaged with first engagement device 1208 and/or may want to engage with first engagement device 1208 in a different mode of operation. Entity 1204 may combine first engagement device with one or more engagement device modifiers. An "engagement device modifier" as used in this disclosure is any object or group thereof that changes an operation of an engagement device. In some embodiments, system 1200 may include first engagement device modifier 1212. First engagement device modifier 1212 may include any apparatus as described above. In some embodiments, system 1200 may include second engagement device modifier 1216. Second engagement device modifier 1216 may include any apparatus as described above. In some embodiments, system 1200 may include third engagement device modifier 1220. Third engagement device modifier 1220 may include any apparatus as described above. In some embodiments, an engagement device modifier may oscillate first engagement device 1208 through a field manipulation of a field of first engagement device 1208. An oscillation of first engagement device 1208 may include a rhythmic motion of first engagement device 1208. A "rhythmic motion" as used in this disclosure is a repeating movement of an object. In some embodiments, each engagement device of system 1200 may be configured to operate independently and/or with another engagement device. As a non-limiting example, first engagement device modifier 1212 may combine with second engagement device modifier 1216 and/or third engagement device modifier 1220 which may provide multiple modes of operation for first engagement device 1208. Each engagement device modifier may provide an interaction of first engagement device 1208 for entity 1204. In some embodiments, first engagement device 1208 and/or an engagement device modifier may include a visual engagement element. A "visual engagement element" as used in this disclosure is any optical attribute of an object. In some embodiments, a visual engagement element may include, but is not limited to, paintings, color codes, markings, and the like. As a non-limiting example, first engagement device 1208 may include a first color denoting a first field polarity on a top surface of first engagement device 1208, and a second color denoting a second field polarity on a bottom surface of first engagement device 1208.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 13:
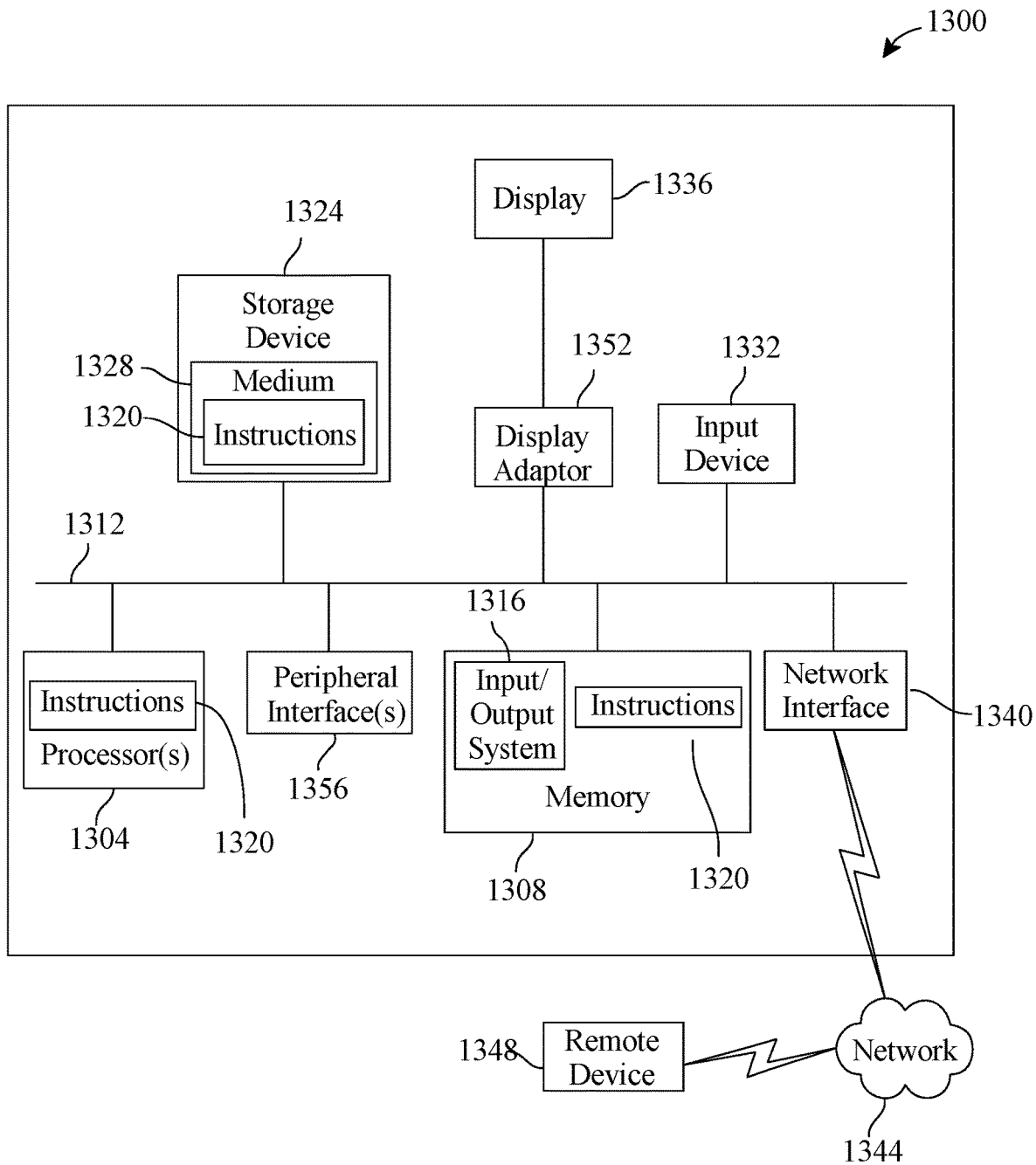
FIG. 13 is a block diagram of a computing system that can be used to implement any one or more of the methodologies disclosed herein and any one or more portions thereof.

FIG. 13 shows a diagrammatic representation of one embodiment of a computing device in the exemplary form of a computer system 1300 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1300 includes a processor 1304 and a memory 1308 that communicate with each other, and with other components, via a bus 1312. Bus 1312 may include any of several types of bus structures including, but not limited to, a memory bus, a memory controller, a peripheral bus, a local bus, and any combinations thereof, using any of a variety of bus architectures.

Still referring to FIG. 13, processor 1304 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1304 may be organized according to Von Neumann and/or Harvard architecture as a non-limiting example. Processor 1304 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Still referring to FIG. 13, memory 1308 may include various components (e.g., machine-readable media) including, but not limited to, a random-access memory component, a read only component, and any combinations thereof. In one example, a basic input/output system 1316 (BIOS), including basic routines that help to transfer information between elements within computer system 1300, such as during start-up, may be stored in memory 1308. Memory 1308 may also include (e.g., stored on one or more machine-readable media) instructions (e.g., software) 1320 embodying any one or more of the aspects and/or methodologies of the present disclosure. In another example, memory 1308 may further include any number of program modules including, but not limited to, an operating system, one or more application programs, other program modules, program data, and any combinations thereof.

Still referring to FIG. 13, computer system 1300 may also include a storage device 1324. Examples of a storage device (e.g., storage device 1324) include, but are not limited to, a hard disk drive, a magnetic disk drive, an optical disc drive in combination with an optical medium, a solid-state memory device, and any combinations thereof. Storage device 1324 may be connected to bus 1312 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1324 (or one or more components thereof) may be removably interfaced with computer system 1300 (e.g., via an external port connector (not shown)). Particularly, storage device 1324 and an associated machine-readable medium 1328 may provide nonvolatile and/or volatile storage of machine-readable instructions, data structures, program modules, and/or other data for computer system 1300. In one example, software 1320 may reside, completely or partially, within machine-readable medium 1328. In another example, software 1320 may reside, completely or partially, within processor 1304.

Still referring to FIG. 13, computer system 1300 may also include an input device 1332. In one example, a user of computer system 1300 may enter commands and/or other information into computer system 1300 via input device 1332. Examples of an input device 1332 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1332 may be interfaced to bus 1312 via any of a variety of interfaces (not shown) including, but not limited to, a serial interface, a parallel interface, a game port, a USB interface, a FIREWIRE interface, a direct interface to bus 1312, and any combinations thereof. Input device 1332 may include a touch screen interface that may be a part of or separate from display 1336, discussed further below. Input device 1332 may be utilized as a user selection device for selecting one or more graphical representations in a graphical interface as described above.

Still referring to FIG. 13, a user may also input commands and/or other information to computer system 1300 via storage device 1324 (e.g., a removable disk drive, a flash drive, etc.) and/or network interface device 1340. A network interface device, such as network interface device 1340, may be utilized for connecting computer system 1300 to one or more of a variety of networks, such as network 1344, and one or more remote devices 1348 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1344, may employ a wired and/or a wireless mode of communication. In general, any network topology may be used. Information (e.g., data, software 1320, etc.) may be communicated to and/or from computer system 1300 via network interface device 1340.

Still referring to FIG. 13, computer system 1300 may further include a video display adapter 1352 for communicating a displayable image to a display device, such as display device 1336. Examples of a display device include, but are not limited to, a liquid crystal display (LCD), a cathode ray tube (CRT), a plasma display, a light emitting diode (LED) display, and any combinations thereof. Display adapter 1352 and display device 1336 may be utilized in combination with processor 1304 to provide graphical representations of aspects of the present disclosure. In addition to a display device, computer system 1300 may include one or more other peripheral output devices including, but not limited to, an audio speaker, a printer, and any combinations thereof. Such peripheral output devices may be connected to bus 1312 via a peripheral interface 1356. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A modular field manipulation apparatus, comprising:
   a central field manipulation device, wherein the central field manipulation device comprises:
   a first surface having a first field polarity; and a second surface positioned opposite the first surface, wherein the second surface has a second field polarity; and at least one interconnecting component, wherein the at least one interconnecting component comprises:

a recess, wherein the recess is configured to physically support the central field manipulation device, wherein the central field manipulation device is configured to move within the recess, and wherein the recess is configured to oscillate the central field manipulation device through opposing magnetic fields; and a tether, wherein the tether is configured to provide a tension to the first surface of the central field manipulation device.

2. The modular field manipulation apparatus of claim 1, wherein the central field manipulation device further comprises a handle.

3. The modular field manipulation apparatus of claim 1, wherein the recess is configured to direct a movement of the central field manipulation device.

4. The modular field manipulation apparatus of claim 1, wherein the at least one interconnecting component modifies an alignment of the first field polarity of the central field manipulation device.

5. The modular field manipulation apparatus of claim 4, wherein the modification of the alignment of the first field polarity of the central manipulation device places the central field manipulation device in an oscillating movement.

* * * * *